(12) United States Patent
Poirier et al.

(10) Patent No.: US 9,920,089 B2
(45) Date of Patent: Mar. 20, 2018

(54) PROCESS FOR PRODUCING A SOLID FORM OF ABIRATERONE ACETATE

(71) Applicant: ZACH SYSTEM, Avrille (FR)

(72) Inventors: Patricia Poirier, Saint Clement de la Place (FR); Yvon Derrien, La Meignanne (FR); Massimiliano Forcato, Avrille (FR); Livius Cotarca, Cervignano del Friuli (IT); Pierrick Morice, Beaucouze (FR)

(73) Assignee: ZACH SYSTEM, Avrille (FR)

( * ) Notice: Subject to any disclaimer, the term of this patent is extended or adjusted under 35 U.S.C. 154(b) by 42 days.

(21) Appl. No.: 14/785,110

(22) PCT Filed: Apr. 11, 2014

(86) PCT No.: PCT/EP2014/057375
§ 371 (c)(1),
(2) Date: Oct. 16, 2015

(87) PCT Pub. No.: WO2014/170221
PCT Pub. Date: Oct. 23, 2014

(65) Prior Publication Data
US 2016/0083416 A1  Mar. 24, 2016

(30) Foreign Application Priority Data
Apr. 19, 2013  (EP) .................................... 13305517

(51) Int. Cl.
*C07J 43/00* (2006.01)
*A61K 9/16* (2006.01)

(52) U.S. Cl.
CPC ........... *C07J 43/003* (2013.01); *C07J 43/006* (2013.01)

(58) Field of Classification Search
None
See application file for complete search history.

(56) References Cited

U.S. PATENT DOCUMENTS

| 2007/0249836 A1 | 10/2007 | Hunt |
| 2010/0152437 A1 | 6/2010 | Hunt |
| 2012/0053340 A1 | 3/2012 | Hunt |
| 2013/0090468 A1 | 4/2013 | Hunt |

FOREIGN PATENT DOCUMENTS

| CN | 101 768 199 A | 7/2010 |
| EP | 0 633 893 A1 | 1/1995 |
| EP | 0 721 461 A1 | 7/1996 |
| JP | 58143832 A * | 8/1983 |
| WO | 2006/021776 A1 | 3/2006 |
| WO | WO 2006/021777 A1 | 3/2006 |
| WO | WO 2013/053691 A1 | 4/2013 |

OTHER PUBLICATIONS

Thorat, Alpana A., and Sameer V. Dalvi. "Liquid antisolvent precipitation and stabilization of nanoparticles of poorly water soluble drugs in aqueous suspensions: Recent developments and future perspective." Chemical Engineering Journal 181 (2012): 1-34.*
Presentation by Robert Strickey of Dec. 1, 2011, entitled "1) Formulations in Drug Discovery: Enabling Preclinical Pharmacokinetic, Pharmacodynamic and Toxicology Studies 2) Pediatric Formulations: Evolving Issue of To Use or Not to Use Preservatives".*
Wang, Zhe, et al. "Preparation of ultrafine beclomethasone dipropionate drug powder by antisolvent precipitation." Industrial & engineering chemistry research 46.14 (2007): 4839-4845.*
Machine translation of CN 101768199 A, original document published Jul. 7, 2010.*
SciFinder abstract of CN 101768199 A, original document published Jul. 7, 2010.*
Derwent abstract of JP 58-143832; original document published Aug. 26, 1983.*
Ghenge, Gokul R., et al. "An overview to spherical crystallization and its evaluation." Int J App Pharm 3.3 (2011): 1-6.*
Machine translation of CN 102558275A, original document published 2012.*
Gerard A, Potter, et al., "A Convenient, Large-Scale Synthesis of Abiraterone Acetate [3β-Acetoxy-17-(3-Pyridyl) Androsta-5,16-Diene], A Potential New Drug for the Treatment of Prostate Cancer" Organic Preparations and Procedures International, vol. 29, No. 1, XP008056111, pp. 123-128, (1997).
International Search Report dated Jul. 7, 2014 for PCT/EP2014/057375 filed on Apr. 11, 2014.

* cited by examiner

*Primary Examiner* — Nissa Westerberg
(74) *Attorney, Agent, or Firm* — Oblon, McClelland, Maier & Neustadt, L.L.P.

(57) ABSTRACT

The present invention relates to a process for the preparation of 17-substituted steroids and, more particularly, to an improved method of preparing micro size abiraterone or derivatives thereof in high yield and purity by means of a spherical agglomeration process.

12 Claims, 1 Drawing Sheet

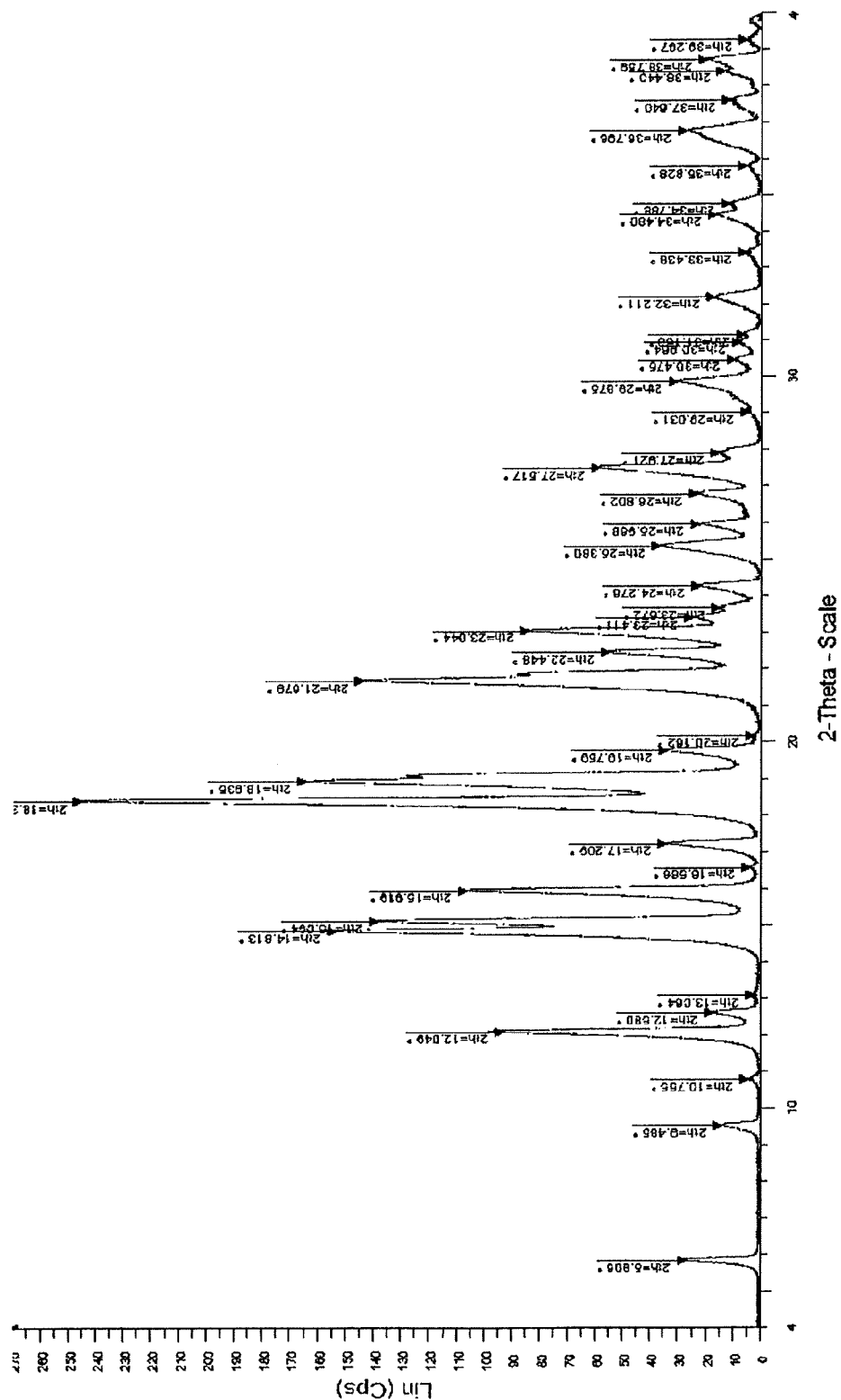

PROCESS FOR PRODUCING A SOLID FORM OF ABIRATERONE ACETATE

The present invention relates to a process for the preparation of 17-substituted steroids and, more particularly, to an improved method of preparing micro size abiraterone or derivatives thereof in high yield and purity by means of a spherical agglomeration process.

BACKGROUND OF THE INVENTION

Abiraterone acetate, chemically designated as (3β)-17-(3-pyridinyl)-androsta-5,16-dien-3-yl acetate of formula

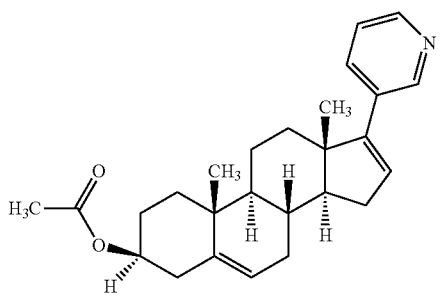

is a prodrug which is converted in vivo to abiraterone, 17-(3-pyridyl)-androsta-5,16-dien-3β-ol.

Abiraterone is a potent inhibitor of human cytochrome $P450_{17\alpha}$, a potential target enzyme in the treatment of hormone-dependent prostatic carcinoma.

Abiraterone acetate is the active ingredient of the approved drug (Zytiga®) which is administered in a solid oral dosage form (250 mg tablet).

Zytiga® in combination with prednisone is indicated for the treatment of patients with metastatic castration resistant prostate cancer (CRPC) who have received prior chemotherapy containing docetaxel.

Literature reports several processes for the preparation of abiraterone or derivatives thereof.

Abiraterone was first described in patent application EP 0633893 (BTG International Ltd.) covering 16,17-ene-17-(3-pyridyl) steroids as a class of compounds useful in the treatment of androgen- and oestrogen-dependent disorders.

Particularly, in the specific experimental work, abiraterone acetate is prepared from dehydroepiandrosterone-3-acetate and, then, converted into abiraterone.

Chromatography is required to give the desired acetyl ester by elution with petroleum-diethyl ether and crystallization from hexane. Abiraterone is obtained by elution with toluene-diethyl ether and crystallization from toluene.

However, it has been observed that the overall yield of the process is low (around 48%) and chromatography appears to be the only tool able to provide a substantially pure product which is, then, crystallised from apolar solvents and, optionally, used in the downstream of the process.

EP 0721461 (BTG International Ltd.) describes an improved method for the preparation of (3β)-acyloxy-16, 17-ene-17-(3-pyridyl) steroids; especially, the preferred compound (3β)-acetoxy-17-(3-pyridyl)-androsta-5,16-diene via acylation of (3β)-hydroxy derivative and crystallization from ethanol/water and, then, hexane is prepared.

However, the estimated overall yield starting from dehydroepiandrosterone is low (around 41%) and, mainly, a final purification by reverse phase chromatography is required.

WO 2006/021776 (BTG International Ltd.) describes novel salt forms of $C_2$-$C_4$ acyl esters of abiraterone or a derivative thereof and to a process for the preparation of abiraterone or a salt or derivative thereof. The preferred salt is abiraterone acetate methanesulfonate which is, preferably, recovered from methyl tert-butyl ether.

WO 2006/021777 (BTG International Ltd.) describes a process for the preparation of abiraterone or $C_2$-$C_4$ acyl esters of abiraterone or a derivative thereof.

Coupling as well as isolation steps to abiraterone acetate are carried out by following the teachings of the International application WO '776 above.

However, the estimated overall yield of the process starting from dehydroepiandrosterone 3-acetate is very low (around 32%) with a purity around 97%; isolation as, inter alia, the mesylate salt entails an additional neutralization and optionally crystallization step(s) with further loss in yield.

Furthermore, Chinese application CN 101768199 discloses abiraterone acetate polymorphs A, B, C and D; methods of preparing said polymorphs comprise re-crystallizing abiraterone acetate from different solvents such as ethanol-hexane or ethanol-water mixtures, ethyl acetate or acetone, isopropanol as well as acetonitrile.

Chinese application CN 102731605 provides for an abiraterone acetate purification method, said method comprises salification of crude abiraterone acetate with phosphoric acid to give a pale yellow crystal, i.e. abiraterone acetate phosphate, neutralization and further recrystallization from methanol yielding the acetate product.

Chinese application CN 102030798 provides for a purification method of abiraterone acetate. The method comprises reacting trifluoromethanesulfonic acid as a salt forming reagent with crude abiraterone acetate to obtain dry abiraterone acetate trifluoromethanesulfonic salt with a purity of over 97%; and performing a neutralization reaction with alkali in dichloromethane to give abiraterone acetate. Chinese application CN 102558275 discloses α-Type abiraterone acetate polymorph; the preparation method comprises dissolving abiraterone acetate in a solvent under heating condition to form a solution, filtering, cooling, crystallizing and drying; solvents used in the method are water, methanol, ethanol, isopropanol, isopropyl ether, acetonitrile, THF, ethyl acetate, chloroform, dichloromethane, toluene, hexane, acetone and mixtures thereof.

Chinese application CN 102321142 discloses abiraterone acetate crystalline form E; the preparation method comprises dissolving abiraterone acetate in a solvent, crystallizing under cooling or water addition and solid separation; solvents used in the method are methanol, ethanol, isopropanol, acetone, acetonitrile and/or THF.

Co-pending international patent application No. PCT/EP2012/069937 in the name of the same Applicant relates to a process for the preparation of 17-substituted steroids and, more particularly, to an improved method of synthesizing abiraterone or derivatives thereof in high yield and purity by means of a key 3β-formyloxy intermediate. Abiraterone is, eventually, crystallized from alcoholic solvents and, optionally, converted into its 3β-acetoxy ester in accordance with known techniques which is, in turn, crystallized preferably from a heptane/ethanol solution.

PURPOSE OF THE INVENTION

Abiraterone acetate is a white to off-white powder practically insoluble in aqueous media (pH range 2.0 to 12.9) very slightly soluble in 0.1N HCl solution and soluble to freely soluble in organic solvents. It is classified as BCS class IV and prepared exclusively as a single polymorphic form, namely, Form A.

EMA Assessment Report for Zytiga® states that the effect on particle size on manufacturability and tablet harness has been evaluated.

Comparative dissolution of tablets manufactured with varying API particle sizes demonstrate that tablet hardness was found to decrease with increasing drug substance particle size and for API D50 controlled between 3-10 μm little effect on dissolution performance could be observed.

Solid state properties of active pharmaceutical ingredients have a decisive impact on dosage form development as well as in vivo performance of the drug. Micrometric properties of drug particles such as shape and size are essential for the formulation of solid dose unit. Particularly, the particle size of poorly soluble ingredients is commonly recognized as an issue due to its impact on dissolution properties. It results from the art that the 16,17-ene-17-(3-pyridyl) steroid derivative, abiraterone acetate, endowed with a specific particle size distribution (PSD) allows to control tablet dissolution performance.

To comply with EMA reported PSD range, micronization is required.

It is known in the art that conventional dry size reduction of pharmaceutical ingredients is accomplished by impact size reduction, especially, via fluid energy impact equipments i.e. by micronizers.

However, said conventional micronization method appears not to be suitable for a reliable and economic industrial application since it suffers from significant cost and procedural drawbacks.

Micronizers are characterized by low efficiency and mechanical stress; high power input during micronization step gives rise to increased free surface energy, electrostatic tendencies and, thus, poor flowability and compressibility of powders which make them difficult to use in downstream processing in the pharmaceutical industry.

Mainly, it is worth noting that abiraterone acetate is a steroid and, thus, confinement issues must be taken into consideration when developing such a fluid energy impact size reduction.

Moreover, micronized particles tend to agglomerate and the increase in surface area is not always reflected in improved dissolution, thus, desired.

Hence, it would be desirable to study improved, efficient methods for preparing pure micro size abiraterone acetate with high yields and under conditions more favourable from the industrial application point of view.

SUMMARY OF THE INVENTION

We have now, surprisingly, found an easy and efficient process to prepare micro size abiraterone acetate via a spherical agglomeration process which allows to overcome the drawbacks of the processes described in the prior art.

The invention is illustrated by reference to the accompanying drawing described below:

The FIGURE shows a powder X-ray diffractogram of abiraterone acetate crystalline Form A according to example 1.

DETAILED DESCRIPTION OF THE INVENTION

The present invention provides for an efficient process to prepare micro size abiraterone acetate via a spherical agglomeration process.

Common techniques for the preparation of micro-size drugs are the mechanical comminution of previously formed larger particles by micronizers or fluid-energy impact equipments.

We have surprisingly found that micro-size abiraterone acetate can be prepared by first precipitating the active ingredient thin crystals out of a solution; agglomerating said crystals in order to isolate them from the reaction mixture; then, disagglomerating by mild milling to get particles endowed with the desired PSD.

The key step of the invention consists essentially in a spherical agglomeration of abiraterone acetate crystals by using a three solvent system. It involves dissolution of abiraterone acetate in a good solvent, crystallization and agglomeration by means of an antisolvent in the presence of a bridging liquid.

Generally, a solution of a compound in a good solvent is poured into a poor solvent which is miscible with the good solvent. The affinity between the solvents must be stronger than the affinity between the good solvent and the compound which causes immediate precipitation of crystals; a third solvent, called bridging liquid, is added in a smaller amount and acts as an interparticle binder that promotes agglomeration. Said bridging liquid, which should not be miscible with the poor solvent and should wet the precipitated crystals, collects the crystals suspended in the system by forming liquid bridges between the crystals due to capillary negative pressure and interfacial tension at the solid-liquid interface.

Therefore, an object of the present invention is a process for preparing micro size abiraterone acetate which comprises:

a) dissolving abiraterone acetate in a polar aprotic solvent;
b) precipitating abiraterone acetate crystals out of the solution by addition of an antisolvent;
c) agglomerating said crystals in the presence of a bridging liquid;
d) isolating the resulting spherical agglomerates of abiraterone acetate crystals; and
e) milling the agglomerates.

Abiraterone acetate is a well known commercially available active pharmaceutical ingredient whose preparation is extensively described in the art.

According to a preferred embodiment of the invention abiraterone acetate is prepared by following the teachings of Co-pending international patent application No. PCT/EP2012/069937 in the name of the same Applicant.

The present invention provides for an efficient process to prepare micro size abiraterone acetate via a spherical agglomeration process.

Abiraterone acetate is first dissolved in a good solvent (step a).

Operatively, abiraterone acetate is contacted with a polar aprotic solvent to give a solution which is optionally maintained at a temperature suitable to avoid crystallization.

Preferred polar aprotic solvents are dimethylacetamide (DMA), dimethylsulfoxide (DMSO) and dimethylformamide (DMF) the latter being the preferred one.

Preferably, the amount of good solvent is comprised between 10-15 l/Kg, more preferably is 12 l/Kg.

Preferably, the concentration of the solution is comprised between 70-90 mg/ml, more preferably is 84 mg/ml.

In a preferred embodiment of the invention the solution obtained in step a) is maintained at a temperature between 25-40° C., preferably around 30° C.

Abiraterone acetate crystals are precipitated out of the solution by addition of an antisolvent (step b).

The general procedure comprises precipitating said crystals by addition of a suitable amount of antisolvent.

In one embodiment of the invention said addition occurs over a period of around 1 hour; the temperature of the reaction mixture is maintained between 15-30° C. to give a thick slurry; and, when the addition is completed, said mixture is kept under stirring for a few minutes at a temperature comprised between 15-30° C.

Preferred antisolvents are water or water in admixture with water miscible organic solvent(s) such as, for instance, methanol, ethanol, isopropanol and acetone; water being preferred.

Preferably, the reaction mixture is kept at a temperature comprised between 20-25° C.

Preferably the amount of antisolvent is comprised between 10-20 l/Kg, more preferably between 12-15 l/Kg.

Preferably, the ratio of the antisolvent with respect to the polar aprotic solvent is comprised between 1 and 1.25 v/v.

Preferably, the solution is added to the antisolvent over a period of around 30 min. to 2 hours, more preferably over a period of 1 hour.

In a preferred embodiment of the invention, a solution of pure abiraterone acetate in dimethylformamide at 30° C. is added to purified water over a period of 1 hour, by maintaining the temperature of the mixture between 20 and 25° C. Abiraterone acetate is precipitated by giving a thick slurry. When the addition is completed, the mixture is stirred for 15 minutes at around 20-25° C.

The crystallization conditions of the invention allows obtaining very thin abiraterone acetate crystals.

Agglomeration occurs in the presence of a bridging liquid (step c).

Operatively, a suitable amount of bridging liquid is added to the organic layer coming from step b) to give spherical agglomerates of abiraterone acetate crystals.

Preferred bridging liquids are ethers such as, for instance, diethyl ether, di-isopropyl ether, cyclopentyl-methyl ether (CPME) and tert-butyl methyl ether (MTBE); the latter being preferred.

Preferably, the bridging liquid is added to the slurry as in step b) over a period comprised between 15 min. to 1 hour, 30 min. being more preferred.

Preferably, the bridging liquid is added to the slurry as in step b) by keeping the temperature of the reaction mixture comprised between 15-30° C., 20-25° C. being more preferred.

Preferably the amount of bridging liquid is comprised between 2-3 l/Kg, more preferably between 2.5-2.7 l/Kg.

Preferably, the ratio of the bridging liquid with respect to the polar aprotic solvent is comprised between 0.21-0.23 v/v.

Preferably, when the addition is completed, the reaction mixture is stirred over a period of 15-30 min.

Preferably, when the addition is completed, the reaction mixture is kept at a temperature comprised between 15-30° C., more preferably between 20-25° C.

In a preferred embodiment of the invention tert-butyl methyl ether is added to the slurry obtained in step b) over a period of 30 minutes by maintaining the temperature at around 20-25° C. When the addition is completed agglomerates are observed. The mixture is then stirred for 15 to 30 minutes at 20-25° C. temperature.

Spherical agglomerates of abiraterone acetate crystals are then isolated (step d).

In one embodiment of the process of the invention, the step d) isolation is carried out by filtration.

Operatively, the slurry coming from step c) is filtered and the resulting solid product is washed with a suitable solvent; the wet solid is, then, dried to give the desired product.

Preferably, said solid product is washed with water; more preferably, several washes are carried out in order to eliminate any residual solvent.

Preferably, said wet solid is dried under vacuum.

Micro size abiraterone acetate is, eventually, obtained by disagglomerating the isolated dry solid (step e).

Operatively, the obtained wet solid is dried under vacuum and, then, milled to give quantitatively abiraterone acetate as very thin particles.

No micronization step by micronizers or fluid-energy impact equipments is required.

In a preferred embodiment of the invention, abiraterone acetate is dissolved in dimethylformamide, then, precipitated by water addition to give a thick slurry which is agglomerated by adding tert-butyl methyl ether.

The filtration of the slurry is very easy. After water washes, the wet solid is dried under vacuum, then, milled to give quantitatively micro size abiraterone acetate.

The micro size abiraterone acetate according to the invention complies with the desired particle size distribution of D(0.5)=3-10 μm.

As above reported, it is known in the art that said specific PSD allows to control tablet dissolution performance.

The agglomerating step c) allows isolating abiraterone acetate crystals from the reaction mixture (thick slurry) prepared according to the precipitation conditions.

Spherical agglomerates of abiraterone acetate crystals obtained by the process according to the invention are, thus, useful intermediates in the preparation of micro size abiraterone acetate.

Since the invention is aimed to prepare few micron-size particles, said agglomerates need to be milled.

The inventors have observed that disagglomeration takes place even during a drying procedure, however, mild milling allows getting a homogeneous suitable particle size distribution.

Therefore, a further object of the invention is a spherical agglomerate of abiraterone acetate crystals obtained by the process of the invention.

It is worth noting that the agglomeration process of the invention does not have an impact on the polymorphic form of the crystals of the active ingredient used as substrate.

Therefore, a further object of the invention is a process for preparing micro size abiraterone acetate as described above wherein spherical agglomerates of abiraterone acetate crystalline Form A are isolated.

It is thus evident how the method object of the invention is suitable for industrial production, and constitutes an efficient and economic synthetic improvement for the preparation of abiraterone and derivatives thereof.

To the best of the inventors' knowledge, the spherical agglomeration process carried out on abiraterone acetate is neither known in the art nor suggested by any prior art reference.

The inventors have developed an original method which avoids micronization via conventional physical means i.e. by micronizers or fluid-energy impact equipments and allows obtaining the API, abiraterone acetate, complying with the suitable particle size distribution range (D50 between 3-10 μm).

The product is obtained in quantitative yields and with very high purity; no change of the solid polymorph form as well as the quality profile during and after the agglomeration process of the invention is observed.

Combined precipitation and spherical agglomeration according to the invention allows isolating abiraterone acetate by means of common techniques such as filtration; then, disagglomeration by mild milling allowed the inventors to prepare the active ingredient in batch as a very thin crystalline solid endowed with the desired PSD and without any high energy physical stress.

In substance, the process of the invention provides for:
a) quantitative conversion into highly pure spherical agglomerates;
b) easy and efficient isolation of the API;
c) no micronization by micronizers or fluid-energy impact equipments needed;
d) higher efficiency in terms of feed/mill rate (kg/h) for specific API;
e) controlled PSD distribution (3-10 µm);
f) reduced physical stress of particles;
g). reduced confinement concerns; and
h) no polymorphic conversion concerns.

A practical embodiment of the process object of the present invention comprises solubilising abiraterone acetate in a polar aprotic solvent; precipitating it by antisolvent addition to give a thick slurry; agglomerating said slurry by addition of a bridging liquid; filtrating and washing; so obtained wet solid is dried under vacuum, then, milled to give quantitatively micro size abiraterone acetate as very thin particles [D(0.5)=3-10 µm].

A preferred practical embodiment of the process object of the present invention comprises solubilising abiraterone acetate in DMF; said solution is maintained at around 30° C.; said solution is, then, added to purified water in around 1 hour by maintaining the temperature of the mixture at around 20-25° C. to give a thick slurry; MTBE is then added in around 30 min. by maintaining the temperature of the slurry at around 20-25° C.; slurry is, then, filtered and the solid washed with water; so obtained wet solid is dried under vacuum and, then, milled to give quantitatively micro size abiraterone acetate as very thin particles [D(0.5)=3-10 µm].

For better illustrating the invention the following example is now given.

Example 1

A solution of 16 g of pure abiraterone acetate in 192 ml of dimethylformamide, maintained at 30° C., was added to 192 ml of purified water over a period of 1 hour, maintaining the temperature of the mixture between 20 and 25° C. Abiraterone acetate was precipitated by giving a thick slurry. When the addition was completed, the mixture was stirred for 15 minutes at 20-25° C. 40 ml of tert-butyl methyl ether were then added to the slurry over a period of 30 minutes, maintaining the temperature at 20-25° C. When the addition was completed, agglomerates were observed. The mixture was then stirred for 15 to 30 minutes at 20-25° C. The slurry was filtered and the solid washed three times with 32 ml of purified water. The wet solid was then dried at 50-55° C. under vacuum to give 15.7 g of dried product which was then milled.

Measured Particle Size Distribution: D(0.5)=4.9 µm
Expected: D(0.5)=3-10 µm
PSD was determined by laser diffraction-dry powder method with a Malvern
Mastersizer 2000 device.

The X-ray diffraction pattern of the milled dried product was measured on a D8 ADVANCE® diffractomer (Brucker) equipped with a Cu K alpha-1 radiation source and a VANTEC-1 detector (Brucker). The diffractogram is shown in the FIGURE and comprises the peaks listed in table 1 below. It can be seen from the diffractogram that micro size abiraterone acetate of example 1 has all the characteristic peaks of abiraterone acetate crystalline form A.

It should be borne in mind that the relative intensity of the X-ray powder diffraction peaks can vary depending upon sample preparation technique, sample mounting procedure and the particular instrument employed.

TABLE 1

| Caption | Angle 2-Theta ° | d value Angstrom | Intensity Cps | Intensity % % |
|---|---|---|---|---|
| 2th = 5.806° | 5.806 | 15.21083 | 26.1 | 10.7 |
| 2th = 9.485° | 9.485 | 9.31672 | 13.2 | 5.4 |
| 2th = 10.755° | 10.755 | 8.21974 | 3.62 | 1.5 |
| 2th = 12.049° | 12.049 | 7.33922 | 92.7 | 37.8 |
| 2th = 12.580° | 12.58 | 7.03074 | 16.4 | 6.7 |
| 2th = 13.064° | 13.064 | 6.77145 | 1.44 | 0.6 |
| 2th = 14.813° | 14.813 | 5.97542 | 153 | 62.5 |
| 2th = 15.094° | 15.094 | 5.86486 | 138 | 56.3 |
| 2th = 15.919° | 15.919 | 5.56284 | 106 | 43.2 |
| 2th = 16.566° | 16.566 | 5.34683 | 2.92 | 1.2 |
| 2th = 17.209° | 17.209 | 5.14872 | 33.5 | 13.6 |
| 2th = 18.387° | 18.387 | 4.8214 | 245 | 100 |
| 2th = 18.935° | 18.935 | 4.68289 | 164 | 66.9 |
| 2th = 19.759° | 19.759 | 4.48945 | 33.1 | 13.5 |
| 2th = 20.162° | 20.162 | 4.4008 | 1.59 | 0.6 |
| 2th = 21.679° | 21.679 | 4.09604 | 143 | 58.5 |
| 2th = 22.448° | 22.448 | 3.95747 | 54.3 | 22.1 |
| 2th = 23.044° | 23.044 | 3.85651 | 83.4 | 34 |
| 2th = 23.411° | 23.411 | 3.79686 | 24.2 | 9.8 |
| 2th = 23.672° | 23.672 | 3.75553 | 14.1 | 5.7 |
| 2th = 24.276° | 24.276 | 3.66342 | 21.5 | 8.8 |
| 2th = 25.380° | 25.38 | 3.50654 | 35.7 | 14.6 |
| 2th = 25.968° | 25.968 | 3.42851 | 21.8 | 8.9 |
| 2th = 26.802° | 26.802 | 3.32361 | 22.4 | 9.1 |
| 2th = 27.517° | 27.517 | 3.23891 | 58 | 23.6 |
| 2th = 27.921° | 27.921 | 3.19294 | 14.6 | 6 |
| 2th = 29.031° | 29.031 | 3.07332 | 3.65 | 1.5 |
| 2th = 29.875° | 29.875 | 2.98835 | 29.6 | 12.1 |
| 2th = 30.475° | 30.475 | 2.93087 | 8.68 | 3.5 |
| 2th = 30.964° | 30.964 | 2.8857 | 6.72 | 2.7 |
| 2th = 31.168° | 31.168 | 2.86732 | 5.21 | 2.1 |
| 2th = 32.211° | 32.211 | 2.77682 | 16.3 | 6.7 |
| 2th = 33.438° | 33.438 | 2.67764 | 4.57 | 1.9 |
| 2th = 34.480° | 34.48 | 2.59905 | 15.6 | 6.4 |
| 2th = 34.788° | 34.788 | 2.57674 | 10.6 | 4.3 |
| 2th = 35.828° | 35.828 | 2.50432 | 4.73 | 1.9 |
| 2th = 36.796° | 36.796 | 2.44065 | 26.5 | 10.8 |
| 2th = 37.640° | 37.64 | 2.38779 | 10.5 | 4.3 |
| 2th = 38.440° | 38.44 | 2.33995 | 12.3 | 5 |
| 2th = 38.759° | 38.759 | 2.3214 | 19.2 | 7.8 |
| 2th = 39.297° | 39.297 | 2.29085 | 4.47 | 1.8 |

Example 2

A solution of 16 g of pure abiraterone acetate in 192 ml of dimethylformamide, maintained at 30° C. to avoid the crystallization, was added to 192 ml of purified water in the presence of abiraterone acetate seed having D(0.5)=6.7 µm, over a period of 1 hour, maintaining the temperature of the mixture between 39° and 44° C. Abiraterone acetate precipitated giving a thick slurry. At the end of the addition, the mixture was cooled down to 20°-25° C. over 15 minutes. 43 ml of tert-butyl methyl ether were then added to the slurry over a period of 30 minutes, maintaining the temperature at 20°-25° C. At the end of the addition, agglomerates were observed. The mixture was stirred for 15 to 30 minutes at 20°-25° C. The slurry was then filtered and the solid was washed three times with 32 ml of purified water. The wet solid was then dried at 50°-55° C. under vacuum to give 15.7 g of dried product after milling.

Particle size measured: D(0.5)=10.7 μm
Expected: D(0.5)=3-10 μm

Example 3

A solution of 12.5 kg of pure abiraterone acetate in 150 l of dimethylformamide, maintained at 30° C. to avoid the crystallization, was added into 150 l of purified water over a period of 1.5 hour, maintaining the temperature of the mixture between 20° and 25° C. Abiraterone acetate precipitated giving a thick slurry. The mixture was stirred for 15 minutes at 20°-25° C. after the end of the addition. 33 l of tert-butyl methyl ether were then added to the slurry over a period of 30 minutes, maintaining the temperature at 20°-25° C. At the end of the addition, agglomerates were observed. The mixture was stirred for 40 minutes at 20°-25° C. The slurry was then filtered and the solid washed three times with 24 l of purified water. The wet solid was dried at 50°-55° C. under vacuum then milled to give 11.25 kg of dry final product.

Measured Particle Size Distribution: D(0.5)=3.7 μm
Expected PSD D(0.5): 3-10 μm

Example 4

A solution of 117.85 kg of pure abiraterone acetate in 1415 l of dimethylformamide, maintained at 30° C. to avoid the crystallization, was added into 1415 l of purified water, over a period of 2.5 hour, maintaining the temperature of the mixture between 20° and 25° C. Abiraterone acetate precipitated giving a thick slurry. The mixture was stirred for 15 minutes at 20°-25° C. after the end of the addition. 310 l of tert-butyl methyl ether were then added to the slurry over a period of 30 minutes, maintaining the temperature at 20°-25° C. At the end of the addition, agglomerates were observed. The mixture was stirred for 45 minutes at 20°-25° C. The slurry was then filtered and the solid washed three times with 24 l of purified water. The wet solid was dried at 50°-55° C. under vacuum then milled to give 110.3 kg of dry final product.

Measured Particle Size Distribution: D(0.5)=6.5 μm
Expected PSD D(0.5): 3-10 μm

The invention claimed is:

1. A process for preparing micro size abiraterone acetate crystalline Form A, comprising:
   dissolving abiraterone acetate in a polar aprotic solvent to form an abiraterone acetate solution;
   adding an antisolvent to the abiraterone acetate solution until abiraterone acetate crystals precipitate;
   adding a bridging liquid to the precipitate whereby spherical agglomerates of abiraterone acetate crystals are obtained, wherein the bridging liquid is an ether selected from the group consisting of diethyl ether, di-isopropyl ether, cyclopentyl-methyl ether and tert-butyl methyl ether;
   isolating the spherical agglomerates of abiraterone acetate crystals; and
   milling the spherical agglomerates of abiraterone acetate crystals.

2. The process according to claim 1, wherein the polar aprotic solvent is selected from the group consisting of dimethyl acetamide, dimethyl sulfoxide and dimethyl formamide.

3. The process according to claim 2, wherein the polar aprotic solvent is dimethyl formamide.

4. The process according to claim 1, wherein the abiraterone acetate solution is maintained at a temperature of 25-40° C.

5. The process according to claim 1, wherein the antisolvent is water or water admixed with one selected from the group consisting of methanol, ethanol, isopropanol and acetone.

6. The process according to claim 5, wherein the antisolvent is water.

7. The process according to claim 1, wherein the precipitating is carried out at a temperature of 20-25° C.

8. The process according to claim 1, wherein the ether is test-butyl methyl ether.

9. The process according to claim 1, wherein the agglomerating is carded out at a temperature of 15-30° C.

10. The process according to claim 1, wherein the isolating is carried out by filtration.

11. The process according to claim 10, further comprising:
   washing and drying the spherical agglomerates of abiraterone acetate crystals.

12. The process according to claim 1, wherein the ratio of the antisolvent with respect to the polar aprotic solvent is 1-1.25 v/v.

* * * * *